(12) United States Patent
Brooks

(10) Patent No.: US 6,932,976 B2
(45) Date of Patent: Aug. 23, 2005

(54) ENZYME BLOCKING SKIN PROTECTANT CREAM

(75) Inventor: JoAnn Brooks, Arlington, TX (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 85 days.

(21) Appl. No.: 10/215,906

(22) Filed: Aug. 8, 2002

(65) Prior Publication Data
US 2004/0028708 A1 Feb. 12, 2004

(51) Int. Cl.[7] .............. A61K 7/00; A61K 7/42; A61K 31/74; A61K 33/32; A61K 31/355
(52) U.S. Cl. ............ 424/401; 424/59; 424/78.03; 424/78.05; 424/400; 424/642; 514/458; 514/786; 514/865
(58) Field of Search ................ 424/400, 642, 424/401, 59, 78.03, 78.05; 514/458, 786, 865

(56) References Cited

U.S. PATENT DOCUMENTS

| | | | | |
|---|---|---|---|---|
| 4,556,560 A | * | 12/1985 | Buckingham | 424/641 |
| 5,425,954 A | * | 6/1995 | Thompson et al. | 424/401 |
| 5,525,346 A | * | 6/1996 | Hartung et al. | 424/402 |
| 5,658,559 A | * | 8/1997 | Smith | 424/78.02 |
| 6,193,956 B1 | * | 2/2001 | Liu et al. | 424/45 |
| 6,217,890 B1 | * | 4/2001 | Paul et al. | 424/402 |
| 6,464,965 B1 | * | 10/2002 | Chiarelli et al. | 424/59 |
| 6,558,710 B1 | * | 5/2003 | Godfrey | 424/642 |
| 6,649,175 B1 | * | 11/2003 | Haslwanter et al. | 424/401 |
| 6,709,663 B2 | * | 3/2004 | Espinoza | 424/401 |
| 2002/0090386 A1 | | 7/2002 | Haslwanter et al. | |

FOREIGN PATENT DOCUMENTS

| | | |
|---|---|---|
| WO | WO 94/14413 A1 | 7/1994 |
| WO | WO 00/40255 A1 * | 7/2000 |
| WO | WO 01/66075 A1 | 9/2001 |
| WO | WO 01/74294 A2 | 10/2001 |
| WO | WO 01/85128 A2 | 11/2001 |

OTHER PUBLICATIONS

Database WPI, Section Ch, Week 200054, Derwent Publications Ltd., London, GB, Class A96, AN 2000-572607, XP002258952 & CN 1 141 774 A (Cai, H.), Feb. 5, 1997, Abstract, 1 page.

* cited by examiner

*Primary Examiner*—Gary Kunz
*Assistant Examiner*—Marina Lamm
(74) *Attorney, Agent, or Firm*—Brinks Hofer Gilson & Lione

(57) ABSTRACT

The present inventions relate to novel skin protectant creams and the use of such creams to cleanse, treat, and protect skin. The skin protectant creams can be topically applied to protect skin from irritants, to block the action of irritants such as enzymes, and to treat skin that has been subject to irritants. The creams can be applied manually or incorporated into disposable applicators, such as wipers or swabs. The skin protectant creams of the present invention are particularly useful in the prevention of severe skin breakdown which can lead to partial thickness skin wounds.

13 Claims, No Drawings

ENZYME BLOCKING SKIN PROTECTANT CREAM

FIELD OF THE INVENTION

The invention relates to skin protectant creams and the use of such creams to cleanse, treat, and protect the skin of a human. More particularly, the invention relates to a skin protectant cream that can be topically applied to protect skin from irritants, to block the action of irritants, and to treat skin that has been subject to irritants. The present invention is particularly useful in the prevention of severe skin breakdown which can lead to partial thickness skin wounds.

BACKGROUND OF THE INVENTION

The skin is a natural barrier to the penetration of foreign substances. The stratum corneum is the superficial cornified layer of the skin that provides a barrier to water evaporation and reduces the permeation of undesirable molecules from the external environment. The stratum corneum consists of dead cells called corneocytes, which are embedded in a lipid-rich matrix of fatty-acids, ceramides, and cholesterols. This structure of corneocytes embedded in lipids is thought to provide many of the barrier properties of the skin. Substances deposited on the skin must traverse this structure through a tortuous path to gain access to the underlying viable layers of the skin. Skin inflammation occurs when substances which are irritating to the skin are able to penetrate this barrier and initiate an elaborate cascade of immunological events once they contact the skin cells in the viable epidermis and dermis layers. As the skin barrier is compromised, skin is subject to inflammatory events from percutaneous absorbtion of irritants through the stratum corneum.

Skin barrier function can be compromised by a variety of insults that cause inflammation. Insults to the skin, can include, but are not limited to, environmental irritants, mechanical abrasion, continuous tissue load pressure, exposure to body fluids and waste, and exposure to chemicals. For example, physical and chemical treatments, abrasion, tape stripping, ultrasonics, electrical fields, enzymes, solvents, surfactants, and elevated ambient humidity are known to diminish skin barrier function. Bodily fluids and wastes may contain skin irritants in the form of enzymes such as proteases, ureases, and lipases. Enzymes found in feces cleave the stratum corneum proteins and cause the breakdown of the natural barrier of the skin. Bacterial ureases on the skin convert the urea in urine to ammonia resulting in an alkaline pH on the skin. Prolonged exposure of the skin to these enzymes is thought to be a major cause of skin damage that leads to dermatitis and subsequent skin breakdown. In addition, the care of skin in individuals with ostomies is difficult due to the frequent contact of digestive enzymes with skin surrounding the ostomy site. These enzymes can degrade the skin surface and cause severe skin breakdown and partial thickness wounds.

A number of approaches are known for protecting the skin against the action of skin irritants and subsequent skin breakdown. Examples include protective apparel, skin protectant formulations, and anti-inflammatory compositions. Protective apparel garments may prevent irritants from contacting the skin, or may be used to prevent dissemination of irritants from bodily fluids to the surrounding environment, for example, diapers or adult incontinence garments. However, the use of barrier materials in these garments prevents movement of moisture and air and therefore, proliferates an environment in which skin may be kept in contact with the irritants and increase the damage.

Many of the skin protectant formulations commercially available may not provide adequate protection against skin irritants. Many of these formulations consist of softening creams and hydrating compounds to replenish the moisture content of the skin. However, these formulations do not block the irritants present in urine, feces, or blood such as, for example, the proteolytic enzymes present in feces. Furthermore these compositions often consist of petrolatum, lanolin or greasy compounds that can rub off onto garments and decrease the absorbency of the garment.

Another method of treating skin irritation is the topical use of anti-inflammatory compounds. However, the topical use of anti-inflammatory compounds does not protect the skin from coming in contact with an irritant, therefore, damage to the skin still occurs. The anti-inflammatory substance mitigates the inflammatory response but it does not prevent the skin damage that elicits the inflammatory event in the first place.

What is needed in the art is a skin protectant cream that can be applied directly to the skin to provide a barrier from contact with irritants, block the activity of enzymes found in bodily fluids and feces, and can enhance the barrier properties of the skin. What is also needed in the art is a skin protectant cream that will remain on the skin to continue to provide a barrier, block the activity of enzymes, and replenish the barrier properties of the skin. What is also needed in the art are disposable application articles to apply the skin protectant cream. These and other needs are provided by the present invention.

SUMMARY OF THE INVENTION

The invention relates to enzyme blocking skin protectant creams for topical application to the epidermal surface of a human. The skin protectant creams comprise at least one barrier compound for preventing access of irritating molecules to the epidermal surface, an enzyme blocking compound, and a skin replenishing compound. The barrier compound, the enzyme blocking compound, and the skin replenishing compound are combined in an oil-in-water emulsion. Such skin protectant creams can be provided in formulations comprising creams.

In other aspects of the invention, disposable applicators are provided for topical application of a skin protectant cream to the epidermal surface of a human for cleansing, treating, and protecting the skin. Such applicators can include a substrate upon which the cream is uniformly distributed on at least one surface of the substrate. The applicators can be designed to cleanse the skin and provide a protective residue on the skin.

In another aspect of the invention, a method for treating human skin comprises coating the skin with a pharmaceutically effective amount of a skin protectant cream that comprises at least one barrier compound for preventing access of irritating molecules to the epidermal surface, an enzyme blocking compound, and a skin replenishing compound. The barrier compound, the enzyme blocking compound, and the skin replenishing compound are combined in a stable oil-in-water emulsion which can be in the form of a viscous cream.

DETAILED DESCRIPTION OF THE INVENTION

Skin protectant creams, disposable applicators containing a skin protectant cream, and methods of use are provided for topical administration to the skin of a human, to protect the skin from irritants and restore the natural integrity of the skin. The skin protectant creams are capable of maintaining the pH of the skin, blocking or inhibiting the activity of harmful enzymes, and replenishing the natural barrier. The skin protectant cream of the present invention comprise a barrier compound, an enzyme blocking compound, and a skin replenishing compound, provided in an oil-in-water emulsion that can be used for direct application to the skin, or alternatively, applied to a surface of a disposable applicator for application to the skin. The skin protectant cream of the present invention can be a basic white color in appearance. Formulations for the skin protectant cream comprise creams suitable for topical application.

The barrier compounds of the present invention can be any water proofing compound or water repelling compound that remains on the skin and continues to be effective after contact with skin irritants. The barrier compound is designed to form a thin, tenacious, substantially continuous barrier over the skin to inhibit, or at least minimize the effect of skin irritants. Advantageously, the barrier compound can be a water repelling polymer. In the present invention the barrier compound comprises a polymeric backbone which is designed to repel water from the skin and will prevent the composition from being washed away. Examples of suitable barrier compounds include, but are not limited to, PVP/Hexadecene Copolymer, PVP/Eicosene Copolymer, Acrylate C10–30 Alkyl Acrylate Crosspolymer, Bis-Diglyceryl Polyacyladipate-2, Tricontanyl PVP, and Dimethicone. Polymers suitable for the present invention include, but are not limited to, compounds that are available commercially, for example, Ganex V-216 available from International Speciality Products, Wayne, N.J. or Dimethicone 200 silicone fluid available from Dow Corning of Midland, Mich. Such compounds can be present in a range from about 0.1% to about 2.0% by total weight of the composition.

The present invention comprises enzyme blocking compounds that prevent skin irritation by blocking urease and the enzymes in feces and body fluids that can cause the breakdown of the natural protective barrier of the skin. The enzyme blocking compounds of the present invention can have inhibitory activity against proteolytic and/or lipolytic enzymes including, but not limited to, lipase, carboxypeptidase A, chymotrypsin, elastase, trypsin, leucine aminopeptidase, and bacterial ureases.

Enzyme blocking compounds suitable for the present invention can include any zinc compound that is soluble in the oil-in-water emulsion and will not de-stabilize the emulsion. Advantageously, these compounds include, but are not limited to, zinc sulfate, zinc chloride, zinc oxide, zinc lactate, or combinations thereof. The zinc compound is present in a range from about 0.01% to 3% by weight of the composition. Preferably the zinc compound is present in a range from about 0.25% to about 1% by weight of the composition.

Skin replenishing agents contribute to structural integrity and elasticity. Skin replenishing compounds include, but are not limited to, emollients, vitamins, plant extracts, biochemical cofactors, or combinations thereof.

Emollients are natural or synthetic compounds that soften, sooth, coat, lubricate or moisturize the skin. Emollients include, but are not limited to, fats, butters, waxes, oils, esters, or triglycerides. Emollients suitable for the present invention include sunflower seed oil, caprylic/capric triglyceride, or shea butter. Such compounds are commercially available, for example, from Lipo Chemicals, Patterson, N.J.

Emulsion stabilizers can be used to maintain the oil-in-water emulsion. Advantageously, stabilizers of the present invention can include fatty alcohols or polymers. In one aspect of the invention, fatty alcohols can be used to stabilize the emulsion and provide acceptable viscosity. Examples of fatty alcohols include, but are not limited to, stearyl alcohol, cetearyl alcohol, myristyl alcohol, behenyl alcohol, arachidic alcohol, isostearyl alcohol, isocetyl alcohol, or combinations thereof.

The water employed in the skin protectant cream of the present invention is purified water obtained, for example, by triple osmosis or other acceptable water purifying techniques known in the art.

The present invention can also include other conventional additives such as fragrance, preservatives, preservative adjuvants, or vitamins. Vitamins can include vitamins A, E, C or provitamin B-5. Commercially available vitamins include Dex-Panthenol, Tocopheryl Acetate, or Retinyl Palmitate available from Roche of Nutley, N.J., or Magnesium Ascorbyl Phosphate available from Beacon, Kenilworth, N.J.

For administration to the skin of a human, the compositions will often be formulated to contain one or more preservatives. Preservatives that are suitable for the present invention include, but are not limited to, methylparaben, propylparaben, diazolidinyl urea, or combinations thereof. A commercially available preservative includes Germall II from Sutton Labs, Wayne, N.J. Advantageously, preservative adjuvants can also be used for the present invention. For example, EDTA is a suitable preservative adjuvant that is also a chelating agent which can bind enzymes.

It is believed that a low pH is best to block the enzyme activity in fluids. The proteases which are present in feces and urine have an active pH range of 8.0 to 8.5. Without wishing to be bound by any particular theory, it is believed that an advantage of the present invention is that the lower pH of the cream decreases the activity of the enzymes. The pH of the present invention is preferably in a range from about 4.0 to about 5.5. Most preferably, the pH is in a range from about 4.2 to about 4.5.

Optionally, fragrances can be incorporated into the creams of the present invention. Advantageously, the fragrance selection is light and fresh and in a quantity that does not irritate fragile skin. Preferably the fragrance is a light fresh green floral. The amount of fragrance can be present in a range from about 0.02% to about 0.09%. Fragrances are commercially available from International Flavors and Fragrance, New York, N.Y.

The skin protectant creams formulated for administration to the skin are administered to a human as a preventative treatment to block enzyme activity that may result in damaged skin due to contact with feces or urine. The creams are administered in an amount sufficient to allow inhibition of further damage and are more effective than if the individual were not treated. Amounts adequate to accomplish these effects are defined as a "therapeutically effective dose" and will vary according to the application and the individual.

The skin protectant creams of the present invention can be used as cleansing agents, treating agents, and/or as a prophylactic for the skin of those individuals who may be susceptible to skin irritation by the enzymes present in feces, urine or body fluids. In these uses, the precise amounts again depend on the amount of protection desired and the extent and conditions under which the skin is exposed to potentially damaging conditions, such as those caused by urease, fecal proteases and other irritating body fluids. Single or multiple applications of the skin protectant cream can be carried out daily or over a prolonged period of time. Applications can be repeated as needed and up to about six times daily. Preferably, the applications can be from about 1 to about 4 times daily. The cream can be manually applied directly to the skin by the care recipient or a caretaker. Alternatively, the cream can be applied using a disposable applicator comprising a surface upon which the cream has been pre-applied. Such absorbent articles include, but are not limited to, swabs, wipers, and pads. The cream can also be pre-applied to a surface of a web of woven or nonwoven absorbent material for use as a means to cleanse, treat and protect the skin. The swab, wiper or pad is preferably free of lint.

The skin protectant creams can be pre-applied uniformly and consistently to the surface of disposable applicators using any method known in the art, and can be subsequently packaged for later use at a convenient time. For purposes of the invention, the term pre-applied refers to any manufacturing process that would apply the cream to the surface of the applicator, although the cream could be applied manually to a disposable applicator prior to use.

Alternatively, the disposable applicator can be a wiper comprising any suitable substrate capable of providing an economical coherent fibrous web, including, but not limited to, natural or synthetic materials such as cotton, rayon, polyester, Dacron™, viscose, wood pulp, and combinations thereof. The wiper can comprise tissue, such as creped or uncreped tissue, coform products, hydroentangled webs, airlaid mats, fluff pulp, nonwoven webs, woven webs and composites thereof. Such wipers are known in the art. Especially suitable are those wipers disclosed in patents issued to Kimberly Clark Worldwide.

In another aspect of the invention, the disposable applicator can be a swab comprising fibers, a web, a sponge, a matrix, or a combination thereof. Preferably the swab can comprise hydroentangled, air-entangled, or air-laid fibers arranged in a pad. Airlaid material can be formed by metering an airflow containing the fibers and other optional materials, in substantially dry condition, onto a typically horizontally moving wire forming screen. Suitable systems and apparatus for air-laid mixtures of fibers and thermoplastic material are known in the art.

Advantageously, swabs of the present invention can be in the form of a flat sheet-like pad in various sizes and configurations. Alternatively, swabs can be in the form of strips, or can be wound into an ovoid form or a round form. Swabs can comprise various handles, such as the wooden or plastic stick of the familiar cotton swab used for cosmetic and infant care, or strips that can be folded or grasped for convenient handling. The methods of making such swabs are known in the art. Preferably, the swab of the present invention comprises an oval swab. Also preferably, the swab comprises a size of about 3×5 inches. Most preferably, the swab comprises a size of about 2×3 inches.

In addition to the article itself, typically the packaging in which the disposable article is distributed is also made from a water-barrier, specifically water-resistant, material. Water-resistivity is necessary to prevent the degradation of the packaging from environmental conditions and to protect the disposable articles therein.

This invention is further illustrated by the following examples, which are not to be construed in any way as imposing limitations upon the scope thereof. To the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Nonionic Oil-in-Water Skin Protectant Cream

Oil phase ingredients and water phase ingredients were provided in the amounts listed in the following tables.

|  | % of Total Weight |
|---|---|
| Water Phase Ingredients |  |
| Purified Water | QS to 100% |
| Methylparaben | 0.15–0.25% |
| Disodium EDTA | 0.3–1.0% |
| Dex-Panthenol | 0.2–1.5% |
| Zinc Sulfate | 0.3–1.0% |
| Maleic Acid | 0.03–0.09% |
| Diazolidinyl Urea (below 40 C.) | 0.2–0.3% |
| Beta Glucan | 1.0–2.0% |
| Magnesium Ascorbyl Phosphate | 0.2–0.5% |
| Oil Phase Ingredients |  |
| Dimethicone | 1.0–2.0% |
| Cetearyl Alcohol | 0.3–1.5% |
| Steareth-2 | 1.0–1.6% |
| Steareth-21 | 1.0–1.6% |
| PEG-40 Stearate | 0.5–1.5% |
| Tocopheryl Acetate | 0.1–0.3% |
| Propylparaben | 0.1–0.15% |
| PVP/Hexadecene Copolymer | 0.8–1.8% |
| Shea Butter | 1.0–2.5% |
| Caprylic/Capric Triglyceride | 2.0–4.0% |
| Caprylic/Capric/Stearic Triglyceride | 2.0–4.0% |
| Finsolve TN | 2.5–4.0% |
| Sunflower Seed Oil | 0.5–1.2% |
| Fragrance | 0.03–0.08% |

The water and oil phases of the formula are heated separately in jacketed kettles and combined in 75° C. with high shear agitation. The resulting emulsion was cooled to 40° C. with slow sweep agitation before adding the heat sensitive preservative and fragrance ingredients. Emulsion preparation procedures are well known to those skilled in emulsion chemistry.

The final skin protectant cream can be dispensed into flexible tubes, bottles, or applied by methods known in the art to oval swabs, wipers, or other disposable applicators.

EXAMPLE 2

The skin protectant cream is pre-applied to a non-woven disposable applicator. A 2×3 inch oval or round swab is provided. The skin protectant cream is applied to the swab by methods know in the art. The swab is packaged and sterilized by suitable methods known in the art.

Although particular aspects of the invention have been described, it would be obvious to one skilled in the art that various other modifications can be made without departing from the spirit and scope of the invention. It is therefore intended that all such changes and modifications are within the scope of the appended claims.

What is claimed is:

1. A skin protectant cream for topical application to an epidermal surface of a human comprising: a) at least one barrier compound comprising about 1% to about 2% dimethicone and about 0.8% to about 1.8% PVP/hexadecene copolymer; b) an enzyme blocking compound comprising about 0.3% to about 1% zinc sulfate; and c) a skin replenishing compound selected from pro vitamin B5, sunflower seed oil, or combinations thereof and further comprising about 2% to about 4% capric/caprylic triglyceride; wherein the at least one barrier compound, the enzyme blocking compound and the skin replenishing compound are combined in a stable oil-in-water emulsion.

2. The skin protectant cream of claim 1, wherein the enzyme blocking compound is soluble in the oil-in-water emulsion and will not destabilize the emulsion.

3. The skin protectant cream of claim 1, wherein the enzyme blocking compound further comprise a compound selected from zinc chloride, zinc oxide, zinc lactate, or combinations thereof.

4. The skin protectant cream of claim 1, wherein the at least one barrier compound further comprise a compound is selected from PVP Copolymer, PVPI Eicosine copolymer, Acrylate C10–30 alkyl acrylate crosspolymer, bis-diglyceryl polyacyladipate-2, tricontanyl PVP, or combinations thereof.

5. The skin protectant cream of claim 1, wherein the pH range is from about 4.0 to about 5.5.

6. The skin protectant cream of claim 1, further comprising a preservative, an emulsion stabilizer, a preservative adjuvant, a vitamin, or combinations thereof.

7. The skin protectant cream of claim 6, wherein the emulsion stabilizer is selected from stearyl alcohol, myristyl alcohol, behenyl alcohol, arachidic alcohol, cetearyl alcohol, isostearyl alcohol, isocetyl alcohol, or combinations thereof.

8. A method for protecting human skin comprising coating the skin with a pharmaceutically effective amount of a skin protectant cream comprising at least one barrier compound comprising about 1% to about 2% dimethicone and about 0.8% to about 1.8% PVP/hexadecene copolymer; an enzyme blocking compound comprising about 0.3% to about 1% zinc sulfate; and a skin replenishing compound selected from pro vitamin B5, sunflower seed oil, or combinations thereof and further, comprising about 2% to about 4% capric/caprylic triglyceride; wherein the at least one barrier compound, the enzyme blocking compound, and the skin replenishing compound are combined in an oil-in-water emulsion.

9. The method of claim 8, wherein the step of coating the skin is repeated from about 1 to about 6 times daily.

10. The method of claim 8, wherein the step of coating the skin is repeated from about 2 to about 3 times daily.

11. A method for protecting the skin of a human comprising: (a) providing a disposable applicator comprising a surface having a continuous uniform coating of a skin protectant cream, wherein the skin protectant cream comprises: a barrier compound comprising about 1% to about 2% dimethicone and about 0.8% to about 1.8% PVP/hexadecene copolymer; an enzyme blocking compound comprising about 0.3% to about 1% zinc sulfate; and a skin replenishing compound selected from pro vitamin B5, sunflower seed oil, or combinations thereof and further comprising about 2% to about 4% capric/caprylic triglyceride, combined in an oil-in-water emulsion; (b) contacting the skin with the disposable applicator to coat the skin with the skin protectant cream; and (c) repeating steps a and b as needed.

12. The skin protectant cream of claim 3, wherein the at least one barrier compound is further comprises a compound selected from bis-diglyceryl polyacyladipate-2, tricontanyl PVP, or combinations thereof.

13. The skin protectant cream of claim 12, wherein the pH range is from about 4.0 to about 4.5.

\* \* \* \* \*